United States Patent [19]
Stuckey

[11] Patent Number: 5,649,541
[45] Date of Patent: Jul. 22, 1997

[54] PATIENT RESTRAINT

[76] Inventor: Judith A. Stuckey, 13629 Catamaran, Corpus Christi, Tex. 78418

[21] Appl. No.: 615,867

[22] Filed: Mar. 14, 1996

[51] Int. Cl.$^6$ .......................................................... A61F 5/37
[52] U.S. Cl. .............................. 128/880; 602/20; 602/22
[58] Field of Search .................................. 128/846, 880, 128/877–879; 602/5, 20, 21, 32–36

[56] References Cited

U.S. PATENT DOCUMENTS

| | | | |
|---|---|---|---|
| 1,268,932 | 6/1918 | Corrigan | 602/36 |
| 3,872,861 | 3/1975 | Tamny | 602/36 |
| 5,027,802 | 7/1991 | Donohue | 602/30 |
| 5,074,291 | 12/1991 | Carter | 602/21 |
| 5,451,203 | 9/1995 | Lamb | 602/36 |

*Primary Examiner*—Michael A. Brown
*Attorney, Agent, or Firm*—G. Turner Moller

[57] ABSTRACT

A patient restraint includes a plurality, preferably three, of finger traps stitched to the end of a long strap. The patient's fingers are inserted into the finger traps so the finger traps constrict in diameter when the ends are pulled. The finger traps are preferably transparent so a nurse can inspect the patient's fingers for signs of poor blood circulation. The strap preferably includes two lengths of fabric material so a bow knot can be tied to a support, such as a bed rail or frame, so the patient's hand cannot reach the throat or the patient's other hand.

12 Claims, 1 Drawing Sheet

FIG. 1 FIG. 2
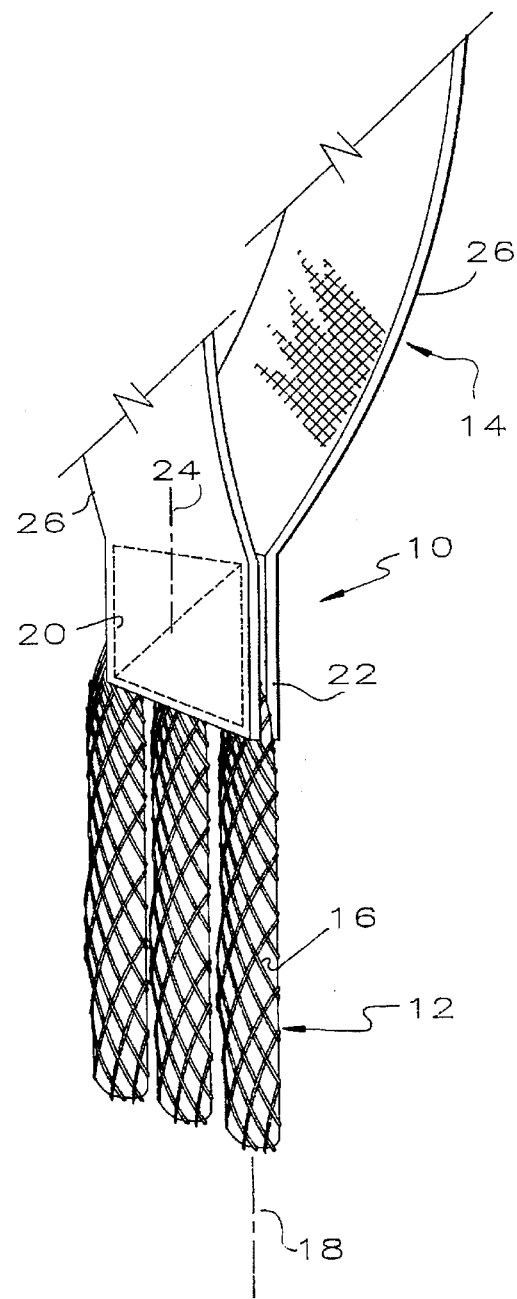
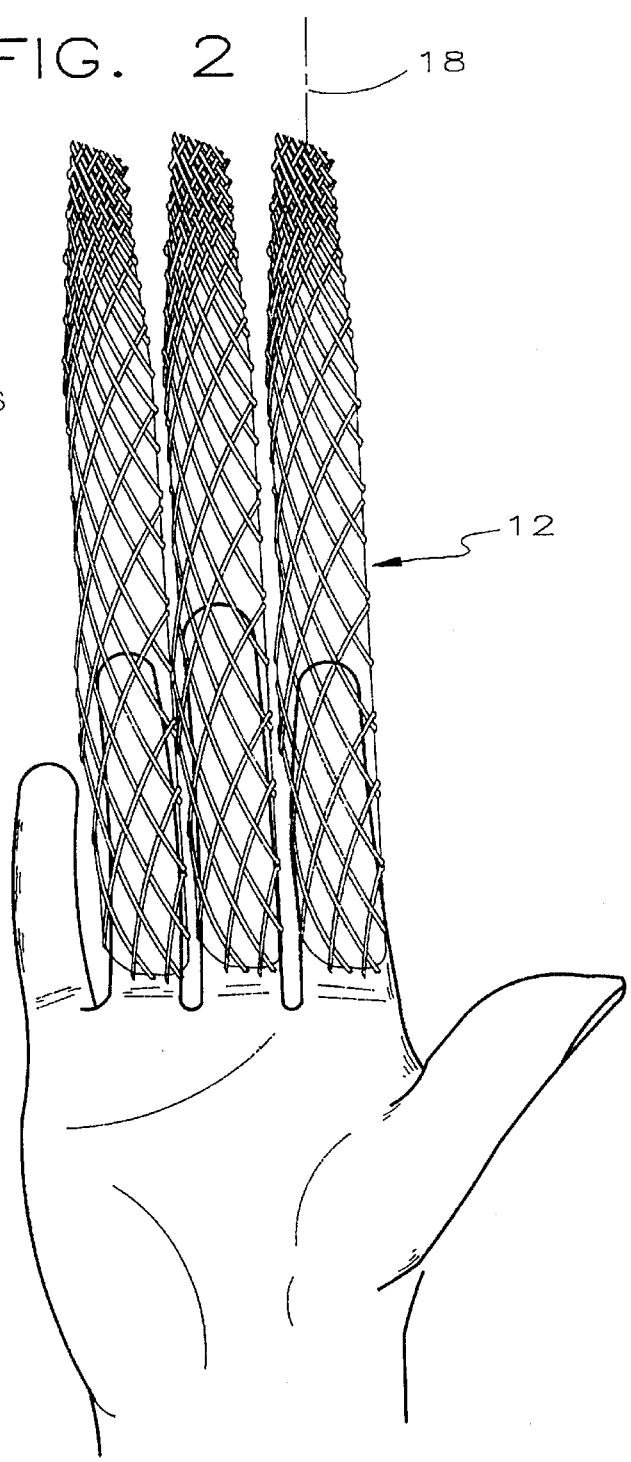
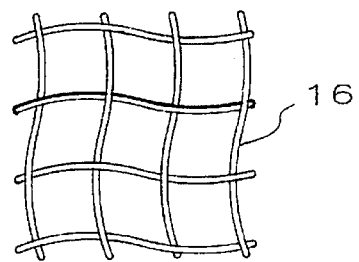
FIG. 3

PATIENT RESTRAINT

This invention is a device used to physically restrain a patient in a hospital environment.

BACKGROUND OF THE INVENTION

This invention relates to a restraining device and, more particularly, to a device for restraining the hands of a medical or surgical patient, typically while the patient is in bed.

There are many common situations in the practice of medicine where the hands of a patient must be restrained for one reason or another. A classic example is a patient in an intensive care unit where a ventilating tube is placed in the patient's throat. These tubes are uncomfortable and, after many hours, can evolve into something excruciating uncomfortable to the point of being nauseating or claustrophobic. It is not uncommon for patients to remove, or attempt to remove, these tubes if their hands are free to do so. The patient might attempt to remove the tube when asleep or unconscious or might attempt it deliberately when conscious. Thus, it is not uncommon to tie a patient's hands to a nearby support, such as a bed rail or the bed frame.

Although a variety of complicated wrist restraints have been proposed in the prior art, such as U.S. Pat. Nos. 1,596,792 and 2,706,477, the current state of the art is a long fabric or tough paper strap. A nurse uses this strap in one of two ways. First, the nurse may simply tie one end of the strap to the patient's wrist and the other end to a bed rail or bed frame. Second, the nurse may tape the strap to the patient's three large fingers with 3" wide adhesive tape. The nurse is sufficiently adept and experienced that the strap is tied to the bed so that neither hand can reach the throat or reach the other hand. There are many problems with both restraint techniques. If the strap is tied to the patient's wrist, it must be tied snugly enough that the strap does not come loose without immediately cutting off blood circulation in the patient's hand. If the strap is tied to the patient's wrist, it may interfere with an IV or with an IV site. Current guide lines require that the straps be removed every two hours and the patient's wrist and hands inspected to determine if circulation to the hand has been interrupted. Concerning tied restraints, this requirement may be observed more in the breach than in the observance. With adhesively attached straps, there is no question that the adhesive tapes are not removed every two hours.

Disclosures of some interest relative to this invention are found in U.S. Pat. 869,686; 2,588,961; 3,122,806 and 5,191,903.

SUMMARY OF THE INVENTION

In this invention, a plurality of finger traps or finger trap sleeves is attached to a long strap. Finger traps are devices most people know from childhood as Chinese handcuffs. They comprise a tube made of woven fabric where the fibers extend helically around the axis of the tube. Fiber trap sleeves have the characteristic of elongating and reducing the diameter in response to a pull on the ends. Thus, in response to a pull on the ends, as by a person trying to pull out of the finger traps, the sleeves grasp the finger more tightly.

Several of the patient's fingers are separately inserted into the finger traps so the sleeves extend past the large knuckle in the finger, technically known as the proximal interphalangeal joint. The long strap is then tied to a bed component, such as a bed rail or the bed frame, so neither patient's hand can reach the throat or reach the other hand.

The restraint of this invention has many advantages. Because the finger trap is not around the wrist, there is no possibility of cutting off circulation to the hand. Because the finger trap does not tightly grip the finger unless the patient pulls on the strap, there is normally no reduction in blood circulation in the finger. Because the finger trap is preferably made of a transparent or translucent material, a nurse looking at the patient's fingers can see whether the finger is pinkish, suggesting good blood circulation in Caucasians, or bluish, suggesting interrupted circulation.

One technique used to determine blood circulation to the fingers is known as blanching. The nurse pinches the fingernail so it turns white. If the fingernail quickly returns to its normal color, blood circulation is good. If the fingernail remains white, blood circulation is poor. Because the finger trap is preferably transparent or translucent, the fingers can be blanched without removing the restraint of this invention.

It is an object of this invention to provide an improved patient restraint.

Another object of this invention is to provide a patient restraint incorporating a one or more finger traps.

These and other objects and advantages of this description will become more apparent as this description proceeds, reference being made to the accompanying drawings and appended claims.

BRIEF DESCRIPTION OF THE DRAWINGS

FIG. 1 is a pictorial view of the patient restraint of this invention;

FIG. 2 is a plan view of a patient hand, palm up, showing the patient restraint of this invention in place; and FIG. 3 is an enlarged view of the fabric of the finger traps of this invention.

DETAILED DESCRIPTION

Referring to FIG. 1, a restraint 10 of this invention comprises a plurality of finger traps or finger trap sleeves 12 attached to the end of a long bodily flexible strap 14 that is capable of being wrapped around and tied to a bed rail, bed frame or the like.

The finger traps 12 are of conventional design known to most people from childhood as Chinese handcuffs. Finger traps are a woven tubular structure comprising a plurality of filaments 16 arranged at a diagonal to the longitudinal axis 18 of the finger trap 12. The finger traps 12 have the capability of contracting in diameter when the ends are pulled so a patient's finger is gripped. A characteristic of conventional finger traps is that the harder the ends are pulled, the more reduction in diameter occurs and the greater the gripping power of the finger traps. Conversely, when the ends are not pulled, there is very little constriction of the finger traps. This is important in the patient restraint of this invention because it reduces any loss of circulation in the patient's fingers.

The filaments of conventional finger traps vary from generally circular modern polymer fibers to generally flat strips analogous to strips of palm fronds. In this invention, any suitable filament type, size and number may be selected although the preferred filament is a generally circular modern polymer filament on the order of about ten mils in diameter. The number of filaments used in the finger traps 12 is also subject to wide variation. Usually, better finger traps have smaller filaments and more of them. Conventional finger traps are available in many styles and patterns from vendors such as Endless Possibilities of Sparta, N.J.

It is much preferred that a nurse can see through the finger traps 12 to inspect the patient's fingers for signs of poor circulation. As used herein, the word transparent is used to describe this ability, whether the finger trap 12 is technically transparent or translucent or whether the finger trap is made of opaque filaments spaced so widely apart that a nurse can see through it. In a preferred embodiment of this invention, this is accomplished by selecting the filament to be a clear, unpigmented polymer, such as polyethylene terephthalate.

It is also much preferred that the finger traps 12 be arranged to expose the ends of the patient's fingers to allow blanching of the fingernails. In this procedure, a nurse squeezes the end of the fingernail. This causes the fingernail to whiten. If the patient suffers from poor circulation, the fingernail remains whitish. If the patient has good circulation, the fingernail shortly returns to its normal color. In the preferred embodiment of this invention where the finger trap 12 is transparent, the patient's fingernails are visible through the finger trap filaments and no special provisions are needed.

It is also preferred to provide the finger traps 12 in two or more nominal diameters to fit patients having different sized fingers. Fortunately, finger traps inherently expand substantially in diameter and only two sizes will fit almost the entire human adult population. Although there is substantial room for selecting the diameter of the finger traps, two suitable sizes are nominally ½" and ¾". This dimension is basically a width, as measured when the tubes are laid flat.

It is much preferred that some indication of the size of the finger trap 12 be incorporated into it. To this end, one fiber 16 in the larger size, for example, may be much darker than the remaining fibers, as suggested in FIG. 3. This feature will immediately show a defect in the restraint 10 if one finger trap 12 is one size and the other finger traps 12 are of a different size.

The patient restraint 10 incorporates at least two finger traps 12 and preferably includes only three. If only one finger trap 12 were to be used, the force applied to the affected finger creates some risk of interrupting circulation to the finger or dislocating the finger if the patient were to become violent. In addition, patients are often left virtually unattended for considerable periods so the provision of two finger traps makes it that much less likely that the patient can remove the finger traps 12. The provision of two finger traps 12 reduces the force applied to each affected finger by spreading the total force between them. Three finger trap sleeves 12 are thought to be optimal by spreading any applied force between three fingers.

The finger traps 12 are attached to the strap 14 in any suitable manner. A preferred manner is to position the finger traps 12 between a pair of fabric swatches and then sew the assembly together with rows of stitches 20. This creates a stiff section 22 where the finger traps 12 join the strap 14. The finger traps 12 are generally parallel to each other and parallel to the axis 24 of the stiff section 22. The strap 14 may be of any suitable material such as fabric or tough reinforced paper. The strap 14 is of a strength to withstand forces applied by the patient and is capable of being wrapped around and tied to a bed rail or bed frame in the same manner as conventional restraints are tied off.

Preferably, the strap 14 comprises two elongate sections 26 with the finger traps 12 between them. Two straps are preferred so bow knots, which are easily untied, may be used. If the strap 14 is the same, or larger, than the width of the finger traps 12, the finger traps 12 may be side-by-side. If the strap 14 is slightly smaller than the width of the finger traps 12, the finger traps 12 may overlap slightly on the inner end thereof and splay slightly outwardly. The elongate strap sections 26 may be of any suitable length and are commonly about the same length as present restraints, usually about 4' long.

As shown in FIG. 2, the finger traps 12 are slipped over the fingers of the patient past the proximal inter-phalangeal joint in a conventional manner. The strap 14 is pulled gently to see if the finger traps 12 are gripping the fingers. The strap 14 is then tied to a support such as a bed rail or bed frame so the hand cannot reach the throat or reach the other hand.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A restraint comprising
   at least two finger traps of an open mesh tubular structure, each having a longitudinal axis, a first end and a second open end for receiving a digit of a person,
   the finger traps, upon application of a tensile force to the ends, being contractible in diameter so as to grip the digit;
   a bodily flexible elongate strap made of a stitchable material capable of being wrapped around and tied to a support and comprising a pair of elongate strap sections having first ends;
   the first ends of the finger traps overlapping the first ends of the strap sections; and
   stitches connecting the first ends of the strap sections together and thereby closing the first ends of the finger traps and connecting the first end of the finger traps to the strap sections, the finger traps being generally parallel and extending generally in the same direction as a long dimension of the strap sections, the second open ends of the finger traps being generally aligned in a plane perpendicular to the finger trap axes.

2. The restraint of claim 1 wherein there are only three finger traps.

3. The restraint of claim 1 wherein an end of the person's digit is visible at a location intermediate the ends of the finger trap.

4. The restrain of claim 1 wherein the elongate strap sections are at least two feet long.

5. The restraint of claim 4 wherein the elongate strap sections are on the order of about four feet long.

6. The restraint of claim 1 wherein the stitchable material is selected from the group consisting essentially of fabric and reinforced paper.

7. The restraint of claim 1 wherein the first ends of the finger traps being positioned between the first ends of the strap sections.

8. A restraint comprising
   at least two finger traps of an open mesh tubular structure, each having a longitudinal axis, a first end and a second open end for receiving a digit of a person,
   the finger trap being transparent intermediate the first and second ends and being made of a plurality of transparent filaments so the person's fingers may be viewed without removing the finger traps;
   the finger traps, upon application of a tensile force to the ends, being contractible in diameter so as to grip the digit;

a bodily flexible elongate tensile member capable of being wrapped around and tied to a support; and means connecting the first end of the finger traps to the tensile member, the finger traps being generally parallel and extending generally in the same direction as a long dimension of the tensile member, the second open ends of the finger traps being generally aligned in a plane perpendicular to the finger trap axes.

9. The restraint of claim 8 wherein at least one of the filaments is pigmented.

10. A method of restraining a human patient having first and second hands, each including a thumb and four parallel fingers, by the use of first and second restraints, each restraint comprising at least two finger traps of an open mesh tubular structure, each having a longitudinal axis, a first end and a second open end for receiving a digit of a person, the finger traps, upon application of a tensile force to the ends, being contractible in diameter so as to grip the digit, a bodily flexible elongate tensile member capable of being wrapped around and tied to a support, and means connecting the first end of the finger traps to the tensile member, the finger traps being generally parallel and extending generally in the same direction as a long dimension of the tensile member, the second open ends of the finger traps being generally aligned in a plane perpendicular to the finger trap axes, the method comprising individually inserting first and second parallel fingers of the patient's first hand in first and second finger traps of the first restraint;

tieing the tensile member of the first restraint to a support;

individually inserting first and second parallel fingers of the patient's second hand in first and second finger trap sleeves of the second restraint; and tieing the tensile member of the second restraint to a support so the patient's second hand is unable to reach the first hand, the patient's second hand being unable to reach the first hand.

11. The method of claim 10 wherein the finger traps are transparent and further comprising the step of blanching at least one end of at least one of the patient's fingers.

12. The method of claim 10 wherein the finger traps are transparent and further comprising the step of visually inspecting the patient's fingers for signs of poor circulation.

* * * * *